(12) United States Patent
Kamihara et al.

(10) Patent No.: US 6,172,230 B1
(45) Date of Patent: Jan. 9, 2001

(54) PROCESS FOR THE PREPARATION OF TETRAHYDRO-INDOLIZINES

(75) Inventors: Shinji Kamihara, Akita; Kazuaki Kanai; Shigeru Noguchi, both of Tokyo, all of (JP)

(73) Assignee: Daiichi Pharmaceutical Co., Ltd., Tokyo (JP)

( * ) Notice: Under 35 U.S.C. 154(b), the term of this patent shall be extended for 0 days.

(21) Appl. No.: 09/147,183

(22) PCT Filed: Apr. 24, 1997

(86) PCT No.: PCT/JP97/01428

§ 371 Date: Oct. 26, 1998

§ 102(e) Date: Oct. 26, 1998

(87) PCT Pub. No.: WO97/41124

PCT Pub. Date: Jun. 11, 1997

(30) Foreign Application Priority Data

Apr. 26, 1996 (JP) .................................................. 8-107251
Apr. 26, 1996 (JP) .................................................. 8-107252

(51) Int. Cl.[7] ...................... C07D 215/00; C07D 221/02
(52) U.S. Cl. ............................................. 546/15; 546/183
(58) Field of Search ........................................ 546/15, 183

(56) References Cited

U.S. PATENT DOCUMENTS

| 4,894,456 | * | 1/1990 | Wall | 546/41 |
| 4,981,968 | * | 1/1991 | Wall | 544/361 |
| 5,106,742 | * | 4/1992 | Wall | 435/233 |
| 5,122,526 | * | 6/1992 | Wall | 514/253 |
| 5,227,380 | * | 7/1993 | Wall | 514/253 |
| 5,244,903 | * | 9/1993 | Wall | 514/279 |
| 5,364,858 | * | 11/1994 | Wall | 514/279 |
| 5,401,747 | * | 3/1995 | Wall | 514/283 |

FOREIGN PATENT DOCUMENTS

WO 90/03169    4/1990   (WO) .

OTHER PUBLICATIONS

Chemical Abstracts 113:211961, 1990.*
Chemical Abstracts 99:70174, 1983.*

* cited by examiner

Primary Examiner—D. Margaret Seaman
(74) Attorney, Agent, or Firm—Oblon, Spivak, McClelland, Maier & Neustadt, P.C.

(57) ABSTRACT

Described is a process for the preparation of Compound (7) in accordance with the following reaction scheme by reacting Compound (5) with ethylene glycol in a solvent in the presence of a Lewis acid, thereby obtaining Compound (6), and then reacting the resulting compound with a carbonate diester in a solvent in the presence of a metal alkoxide ($R^1$, $R^6$ each represents a $C_{1-6}$ alkyl group or the like and $R^5$ represents H or $C_{1-5}$ alkyl group).

Compound (7) so obtained is useful as an intermediate for camptothecins useful as antitumor agents.

22 Claims, No Drawings

PROCESS FOR THE PREPARATION OF TETRAHYDRO-INDOLIZINES

This application is a 371 of PCT/JP97/01428, filed Apr. 24, 1997.

TECHNICAL FIELD

This invention relates to a process for the preparation of an intermediate for the preparation of a camptothecin derivative (refer to Japanese Patent Laid-Open No. HEI 6-87746) useful as an antitumor agent.

BACKGROUND ART

The compound represented by the below-described formula (a) (which will hereinafter be abbreviated as Compound (a). Similar abbreviation will be applied to the compounds represented by other numbers), that is, (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione exhibits excellent antitumor activity and is therefore useful as an antitumor agent (refer to Japanese Patent Laid-Open No. HEI 6-87746).

(a)

The above compound can be obtained, for example, by the below-described synthesis route through the reaction between 8-amino-6-fluoro-5-methyl-2-trifluoroacetylamino-1-tetralone and (4S)-4-ethyl-7,8-dihydro-4-hydroxy-1H-pyrano[3,4-f]indolizine-3,6,10-(4H) trione (refer to Japanese Patent Laid-Open No. HEI 6-87746).

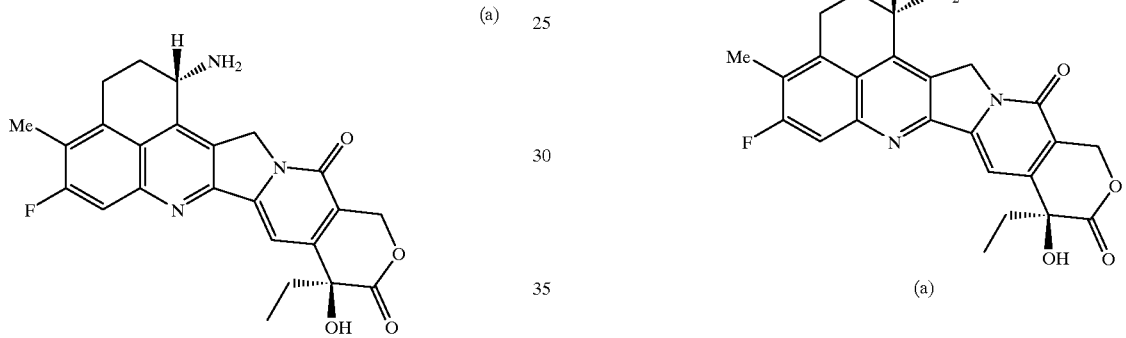

(4S)-4-Alkyl-7,8-dihydro-4-hydroxy-1H-pyrano[3,4-f] indolizine-3,6,10-(4H)-trione (Compound (10)), which is one of the important intermediates for the preparation of the above compound, is known to be prepared, for example, in accordance with the following reaction scheme (J. Med. Chem., 554(1980)).

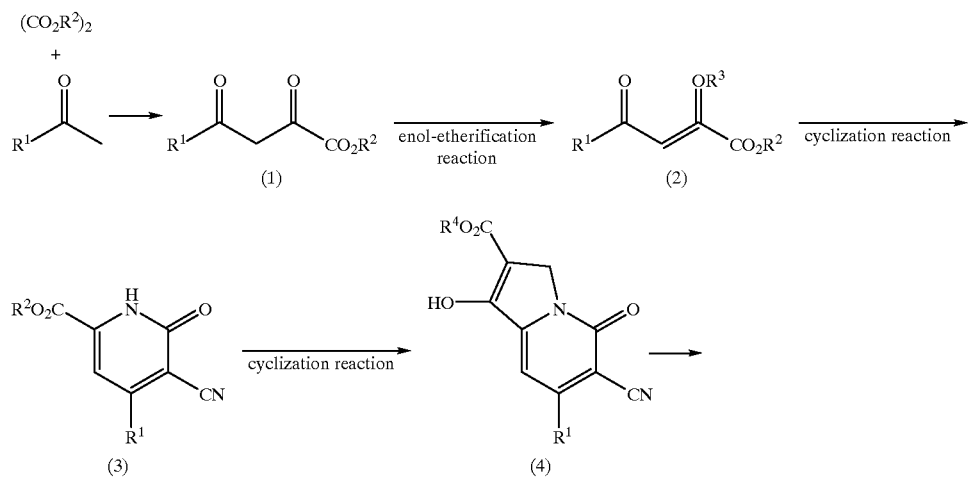

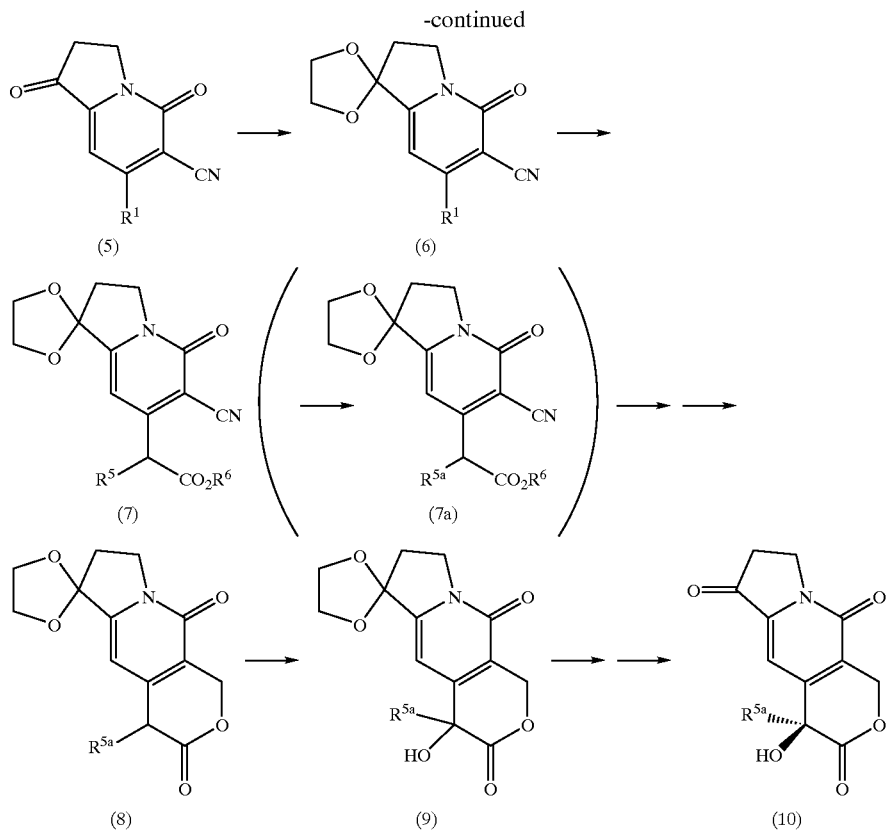

wherein $R^1$ represents a $C_{1-6}$ alkyl group, $R^2$, $R^3$, $R^4$ and $R^6$ each independently represents a $C_{1-6}$ alkyl, aryl or aralkyl group, $R^5$ represents a hydrogen atom or a $C_{1-5}$ alkyl group, $R^{5a}$ represents a $C_{1-5}$ alkyl group; and the reaction in the parentheses is that for obtaining Compound (7a) by alkylating Compound (7) when $R^5$ is a hydrogen atom.

In the above reaction scheme, the reaction for obtaining 6-cyano-1,1-(ethylenedioxy)-7-[(alkoxycarbonyl)-alkyl]-5-oxo-Δ6(8)-tetrahydroindolizine (7) from Compound (1) is reported by Wani et al. (J. Med. Chem., 554(1980)).

The method reported by Wani et al. is however accompanied with the problems such as prolonged reaction time, inferior operability and use of a dangerous reagent. Accordingly, there has been a demand for the development of an industrially superior preparation process.

Described specifically, the enol-etherification reaction for preparing Compound (2) from Compound (1) is effected in the presence of ammonium chloride as a catalyst and it takes even 7 days to complete the reaction. The subsequent cyclization reaction for preparing Compound (3) from Compound (2) is effected using acetone as a solvent, and it takes about 14 hours to complete this reaction. In the next cyclization reaction step for obtaining Compound (4) from Compound (3), dimethylformamide is used as a solvent and it takes as long as 40 hours for the reaction.

The ketalization reaction of Compound (5) is effected in the presence of p-toluenesulfonic acid as a catalyst in a solvent of toluene under azeotropic dehydration with ethylene glycol. This reaction is however accompanied with the problems that the solvent about 80 times the amount of the ketone (5) should be used twice, it takes 20 hours for the completion of the reaction, and the reaction needs cumbersome operation.

In the carbonylation reaction of Compound (6), toluene is used as a solvent and a metal hydride regarded as a dangerous reagent is used as a base. In addition, this step is accompanied with the problems that it includes a dropwise addition step and precipitation of crystals occurs during the reaction, which disturbs stirring.

Accordingly, an object of the present invention is to provide a process for preparing 6-cyano-1,1-(ethylenedioxy)-7-[(alkoxycarbonyl)-alkyl]-5-oxo-Δ6(8)-tetrahydroindolizine (7), which is a synthesis intermediate for the industrial preparation process of a camptothecin derivative (a), within a short time in a convenient manner.

DISCLOSURE OF THE INVENTION

Under such situations, the present inventors have carried out an extensive investigation. As a result, it has been found that Compound (4) can be prepared within a short time in a convenient manner by effecting the reaction from Compound (1) to Compound (4) under specified conditions.

Described specifically, the present inventors have investigated the use of an acid catalyst except ammonium chloride for the enol-etherification reaction. As a result, it has been found that the use of the acid catalyst enables to complete the reaction within about one hour, thereby bringing about a drastic reduction in the reaction time. It has also been found that a change of the solvent for the cyclization reaction to a polar solvent such as dimethyl sulfoxide makes it possible to obtain target Compound (4) from Compound (2) in the same solvent within a short time without isolating Compound (3) or a salt thereof, thereby bringing about a drastic reduction in the reaction time.

It has also been found that by the use of a Lewis acid as a catalyst for the ketalization reaction of Compound (5), the using amount of the solvent can be decreased and the reaction can be completed within about one hour; and that the dropwise addition step can be omitted by using a metal alkoxide having a higher safety as a base for the carbonylation reaction subsequent to the ketalization reaction, thereby bringing about a substantial improvement in the safety and operability, leading to the completion of the present invention.

The process according to the present invention is represented by the following reaction scheme:

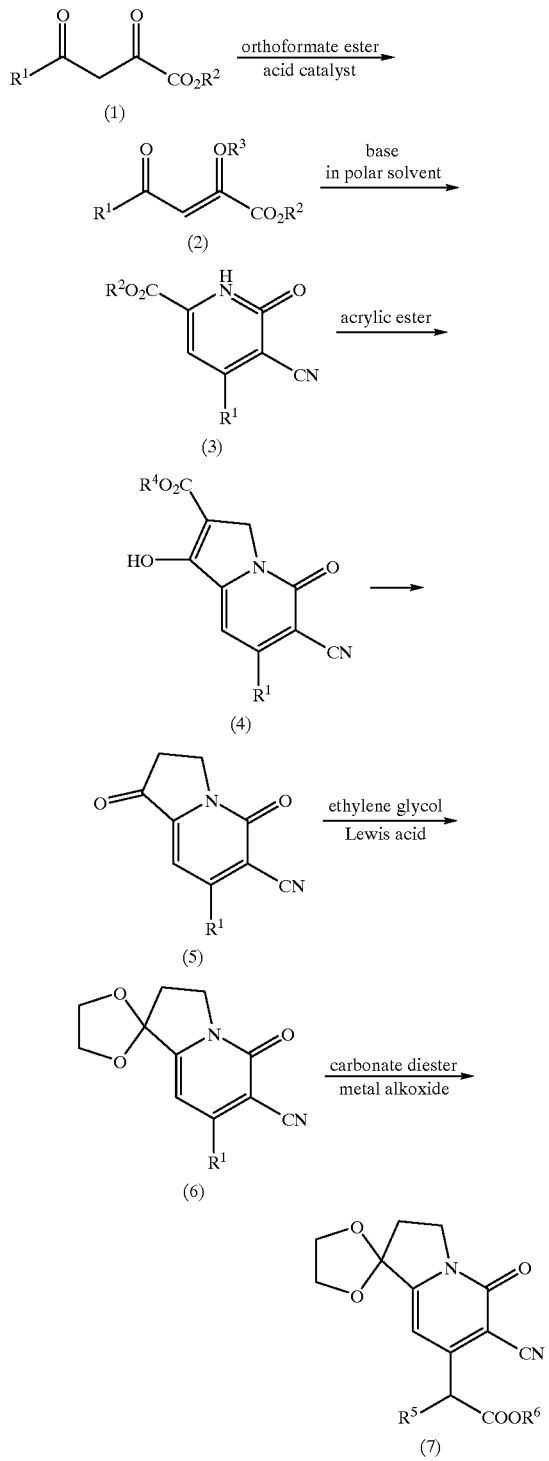

wherein $R^1$, $R^2$, $R^3$, $R^4$, $R^5$ and $R^6$ have the same meanings as defined above.

In the present invention, there is thus provided a process for the preparation of a compound represented by the formula (4), which comprises reacting a compound represented by the formula (1) with an orthoformate ester in the presence of an acid catalyst to obtain a compound represented by the formula (2), reacting the resulting compound (2) with α-cyanoacetamide in a polar solvent in the presence of a base to obtain a compound represented by the formula (3) or salt thereof, then reacting the resulting compound (3) with an acrylic ester.

In the present invention, there is also provided a process for the preparation of a compound represented by the formula (7), which comprise reacting a compound represented by the formula (5) with ethylene glycol in a solvent in the presence of a Lewis acid to obtain a compound represented by the formula (6) and then reacting the resulting compound with a carbonate diester in a solvent in the presence of a metal alkoxide.

BEST MODES FOR CARRYING OUT THE INVENTION

Compound (5) used as a raw material in the present invention may be prepared by the above process, but preparation in accordance with the below-described reaction scheme is industrially advantageous, because the reaction time can be shortened drastically and at the same time, it is possible to effect most of the reaction in one pot.

In the above reaction scheme, $R^1$ represents a $C_{1-6}$ alkyl group and examples of it include methyl, ethyl, n-propyl, isopropyl and n-butyl. $R^2$, $R^3$, $R^4$ and $R^6$ each independently represents a $C_{1-6}$ alkyl group, aryl group or aralkyl group. Examples of the alkyl group include methyl, ethyl, n-propyl, isopropyl and n-butyl. Examples of the aryl group include a phenyl group which may contain one or more than one substituents selected from the group consisting of halogen atoms, $C_{1-6}$ alkyl groups and nitro group. As the aralkyl group, the above-exemplified alkyl group substituted by the above phenyl group can be used and examples include benzyl, substituted benzyl, phenetyl and substituted phenetyl.

Among them, a methyl or n-propyl group is more preferred as $R^1$, with a methyl group being particularly preferred. As $R^2$, $R^3$, $R^4$ or $R^6$, a methyl or ethyl group is more preferred.

Here, Compound (1) can be prepared by the process described in O. S., Coll. Vol. 1, 238(1958), for example, by reacting a ketone such as acetone with an oxalate diester.

First, Compound (1) is subjected to enol-etherification into Compound (2) and this enol-etherification is conducted by reacting Compound (1) with an orthoformate ester in the presence of an acid catalyst. As the acid catalyst usable here, acids stronger than ammonium chloride is preferred. The use of such an acid makes it possible to complete the reaction promptly, thereby shortening the reaction time. Water-free acids are more preferred, with acids equal to or stronger than methanesulfonic acid or toluenesulfonic acid being more preferred. Specific examples include sulfuric acid, sulfonic acids such as methanesulfonic acid and p-toluenesulfonic acid, Lewis acids such as boron trifluoride ether complexes and aluminum chloride; acidic inorganic salts such as calcium chloride, acid resins such as Amberlist; and diatomaceous earth typified by montmorillonite. Among them, methanesulfonic acid and p-toluenesulfonic acid are more preferred, with p-toluenesulfonic acid being particularly preferred. The acid catalyst is preferably used in an amount ranging from 0.005 to 0.1 equivalent (mole) relative to Compound (1), with about 0.01 equivalent being more preferred.

Examples of the orthoformate ester usable in the present invention include $C_{1-6}$ alkyl orthoformates, aryl orthoformates and aralkyl orthoformates, such as methyl orthoformate, ethyl orthoformate, n-propyl orthoformate, isopropyl orthoformate and n-butyl orthoformate, with ethyl orthoformate being particularly preferred. The orthoformate ester is preferably used in an amount ranging from 1 to 10 equivalents (mole) relative to Compound (1), with about 1.1 equivalents being particularly preferred.

It is preferred that the above reaction is carried out in an alcohol solvent, with the reaction in an ethanol solvent being particularly preferred. The solvent is preferably used in an amount ranging from 1 to 50 times (volume/weight) as much as that of compound (1), with 2 times being particularly preferred. The reaction temperature may fall within a range of from room temperature to 60° C., with about 45° C. being particularly preferred. Enol-etherification proceeds within 0.5 hour to several days but is generally completed within about one hour.

The cyclization reaction of Compound (2) thus obtained is conducted by reacting Compound (2) with α-cyanoacetamide in a polar solvent in the presence of a base.

No particular limitation is imposed on the polar solvent usable here insofar as it is a polar solvent inert to the reaction, with a water-free polar solvent being preferred. Usable examples include sulfoxides such as dimethyl sulfoxide and sulfolane, amides such as dimethylformamide, dimethylacetamide and N-methylpyrrolidone, and phosphoric amides such as hexamethylphosphoric triamide. Among them, dimethylsulfoxide is particularly preferred. The solvent is used in an amount ranging from 5 to 50 times (volume/weight) as much as that of Compound (2), with about 10 times being particularly preferred.

No particular limitation is imposed on the base usable in the present reaction. Preferred examples include alkali hydroxide compounds such as sodium hydroxide, potassium hydroxide and lithium hydroxide; and alkali carbonate compounds such as sodium carbonate and potassium carbonate, with potassium carbonate being particularly preferred. The base is preferably used in an amount of 1 to 5 equivalents relative to Compound (2), with 1.5 to 2 equivalents being particularly preferred.

This reaction is carried out at a temperature ranging from room temperature to 95° C., more preferably about 70° C., for 1–24 hours, more preferably about 3 hours.

Compound (3) so obtained exists in the form of a free base and/or salt in the reaction mixture. When Compound (3) is isolated, it is necessary to add a base in order to allow the cyclization reaction by an acrylic ester to proceed. When an acrylic ester is reacted without isolation of Compound (3), on the other hand, it is only necessary to effect the reaction by the addition of an acrylic ester alone without the addition of a base, because the base exists in the reaction mixture or Compound (3) exists in the form of a salt. In other words, it is preferred that an acrylic ester is added to the reaction mixture of Compound (2) and α-cyanoacetamide and the reaction is continued at a similar temperature for a similar period to the above cyclization reaction. Accordingly, the reaction is preferably conducted at a room temperature to 95° C., particularly about 70° C., for 3 to 24 hours, particularly about 6 hours. Incidentally, examples of the acrylic ester usable here include $C_{1-6}$ alkyl acrylates, aryl acrylates and aralkyl acrylates, such as methyl acrylate, ethyl acrylate, isopropyl acrylate, n-propyl acrylate and n-butyl acrylate, with methyl acrylate being particularly preferred.

The acrylic ester is preferably used in an amount ranging from 3 to 20 equivalents (mole) relative to Compound (2), with about 6 equivalents being particularly preferred.

All the reaction steps from Compound (1) to Compound (4) can be carried out continuously as a so-called one pot reaction.

Compound (5) can be obtained by subjecting Compound (4) to decarboxylation. The decarboxylation is performed, for example, by heating Compound (4) to 80 to 110° C. in the presence of acetic acid and concentrated hydrochloric acid.

The reaction to obtain Compound (6) by ethyleneketalization of Compound (5) may be carried out, for example, by mixing Compound (5) with a solvent and a Lewis acid.

No particular limitation is imposed on the kind of the solvent usable here except alcohols, but preferred are those not miscible with water. Examples include chlorinated solvents such as chloroform and dichloromethane, hydrocarbon solvents such as benzene and toluene and solvents such as acetonitrile and nitromethane, with acetonitrile being particularly preferred. The solvent is used preferably in an amount ranging from 10 to 100 times (volume/weight) as much as that of Compound (5), with about 15 times being particularly preferred.

No particular limitation is imposed on the Lewis acid usable in this reaction. Preferred are boron trifluoride, aluminum chloride, titanium tetrachloride and tin tetrachloride, with boron trifluoride being more preferred. The use of boron trifluoride in the form of an ether complex is particularly preferred. The Lewis acid is preferably used in an amount ranging from 5 to 50 equivalents (mole) relative to Compound (5), with about 20 equivalents being particularly preferred.

The reaction temperature preferably falls within a range of from room temperature to 80° C. but the reaction generally proceeds at about 50° C. The reaction time may be 0.5 to 5 hours but the reaction is generally completed within about one hour.

The carbonylation reaction of the resulting Compound (6) into Compound (7) may be conducted, for example, by mixing Compound (6) with a solvent, a metal alkoxide and a carbonate diester.

Examples of the carbonate diester usable here include di-$C_{1-6}$ alkyl carbonates, diaryl carbonates and diaralkyl carbonates, such as dimethyl carbonate, diethyl carbonate, dipropyl carbonate, diisopropyl carbonate and dibutyl carbonate, with diethyl carbonate being particularly preferred.

No particular limitation is imposed on the solvent usable here insofar as it is a solvent inert to the reaction, with water-free one being preferred. Examples include hydrocarbon solvents such as benzene and toluene and ether solvents such as tetrahydrofuran, dioxane, dimethoxymethane, dimethoxyethane, diethoxyethane, diglyme and triglyme. Among them, ether solvents are more preferred, with dioxane and dimethoxyethane being particularly preferred. The solvent is preferably used in an amount ranging from 5 to 50 times (volume/weight) as much as that of Compound (6), with about 10 times being particularly preferred.

No particular limitation is imposed on the metal alkoxide usable here. Examples include alkali metal alkoxides such as sodium methoxide, potassium methoxide, sodium ethoxide, potassium ethoxide, sodium t-butoxide and potassium t-butoxide. Among them, potassium t-butoxide and sodium ethoxide are particularly preferred. The metal alkoxide is preferably used in an amount of 1 to 5 equivalents (mole) relative to Compound (6), with about 1.5 equivalents being particularly preferred.

The carbonate diester is used preferably in an amount ranging from 1 to 10 equivalents (mole) relative to Compound (6), with about 3 equivalents being particularly preferred.

The reaction proceeds at a temperature of from 50 to 120° C., but it generally proceeds at 95° C. to a sufficient degree. The reaction proceeds in 1 to 10 hours, but is, in general, completed sufficiently within about 2 hours.

EXAMPLES

The present invention will hereinafter be described in detail by Examples. It should however be borne in mind that this invention is not limited to or by the following examples.

Preparation Example 1
Ethyl (2-ethoxy-4-oxo)-pent-2-enolate

Ethyl acetopyruvate (1) was prepared in accordance with the process described in the literature (O. S., Coll. Vol. 1, 238(1958)).

To 100 mg of ethyl acetopyruvate (1) were added 0.2 ml of ethanol and 107 mg of ethyl orthoformate, followed by the addition of 0.001 ml of methanesulfonic acid. The resulting mixture was stirred at an external temperature of 55° C. for 2 hours, whereby the title compound was obtained. The product so obtained was not subjected to isolation and purification but exhibited a purity of 93% as a result of gas chromatography.

Preparation Example 2
Ethyl (2-ethoxy-4-oxo)-pent-2-enolate

To 100 mg of ethyl acetopyruvate (1) were added 0.2 ml of ethanol and 107 mg of ethyl orthoformate, followed by the addition of 0.001 ml of sulfuric acid. The resulting mixture was stirred at an external temperature of 55° C. for one hour, whereby the title compound was obtained. The product so obtained was not subjected to isolation and purification but exhibited a purity of 89% as a result of gas chromatography.

Preparation Example 3
Ethyl (2-ethoxy-4-oxo)-pent-2-enolate

To 100 mg of ethyl acetopyruvate (1) were added 0.2 ml of ethanol and 107 mg of ethyl orthoformate, followed by the addition of 2 mg of pyridinium p-toluenesulfonate. The resulting mixture was stirred at an external temperature of 55° C. for 6 hours, whereby the title compound was obtained. The product so obtained was not subjected to isolation and purification but exhibited a purity of 99% as a result of gas chromatography.

Preparation Example 4
Ethyl (2-ethoxy-4-oxo)-pent-2-enolate

To 100 mg of ethyl acetopyruvate (1) were added 0.2 ml of ethanol and 107 mg of ethyl orthoformate, followed by the addition of 0.001 ml of a boron trifluoride-ether complex. The resulting mixture was stirred at an external temperature of 55° C. for 0.5 hour, whereby the title compound was obtained. The product so obtained was not subjected to isolation and purification but exhibited a purity of 99% as a result of gas chromatography.

Preparation Example 5
Ethyl (2-ethoxy-4-oxo)-pent-2-enolate

To 100 mg of ethyl acetopyruvate (1) were added 0.2 ml of ethanol and 107 mg of ethyl orthoformate, followed by the addition of 1 mg of calcium chloride. The resulting mixture was stirred at an external temperature of 55° C. for one hour, whereby the title compound was obtained. The product so obtained was not subjected to isolation and purification but exhibited a purity of 96% as a result of gas chromatography.

Preparation Example 6
Ethyl (2-ethoxy-4-oxo)-pent-2-enolate

To 100 mg of ethyl acetopyruvate (1) were added 0.2 ml of ethanol and 107 mg of ethyl orthoformate, followed by the addition of 5 mg of "Amberlist 15" (acid resin). The resulting mixture was stirred at an external temperature of 55° C. for 2 hours, whereby the title compound was obtained. The product so obtained was not subjected to isolation and purification but exhibited a purity of 97% as a result of gas chromatography.

Preparation Example 7
2-(Methoxycarbonyl)-6-cyano-7-methyl-1,5-dioxo-Δ6(8)-tetrahydroindolizine In 125 ml of ethanol were dissolved 14.2 g of sodium ethoxide, followed by the dropwise addition of a mixed liquid of 25 ml of diethyl oxalate and 13.5 ml of acetone over 20 minutes. The resulting mixture was stirred at room temperature for 3 hours. After the completion of the reaction, water was added to the reaction mixture. Ethanol was then evaporated under reduced pressure. The residue was extracted with chloroform. After the chloroform layer was washed with water, it was dried over anhydrous magnesium sulfate. The solvent was then evaporated, whereby ethyl acetopyruvate (1) was obtained (O. S., Coll. Vol. 1, 238(1958)).

To ethyl acetopyruvate (1) so obtained were added 33.7 ml of ethyl orthoformate, 50 ml of ethanol and 0.4 g of p-toluenesulfonic acid, followed by stirring at an internal temperature of 42 to 44° C. for one hour. To the reaction mixture were then added 15.6 g of α-cyanoacetamide, 25.4 g of potassium carbonate and 250 ml of dimethyl sulfoxide. The resulting mixture was stirred for 3 hours at an internal temperature of 68 to 71° C. To the reaction mixture were added 99 ml of methyl acrylate, followed by stirring for further 6 hours at an internal temperature of 68 to 70° C.

After the completion of the reaction, the reaction mixture was poured into 2 liter of water and they were stirred thoroughly. The reaction mixture was then made acidic with 35 ml of concentrated hydrochloric acid. After the filtration of the crystals so precipitated, they were washed successively with water and methanol. The crude crystals so obtained were stirred in 200 ml of methanol under heating as a slurry, followed by filtration and drying under reduced pressure, whereby 17.6 g of the title compound were obtained.

Preparation Example 8
6-Cyano-7-methyl-1,5-dioxo-Δ6(8)-tetrahydroindolizine

To 10.0 g of the compound obtained in Preparation Example 7 were added 90 ml of acetic acid and 90 ml of concentrated hydrochloric acid, followed by stirring at an external temperature of 120° C. for 2.5 hours. After the completion of the reaction, the solvent was evaporated under reduced pressure. Water was added to the residue. The crystals so precipitated were collected by filtration, followed by washing with water and drying, whereby 6.8 g of the title compound were obtained. The filtration mother liquid was evaporated under reduced pressure. The crystals so precipitated were collected by filtration, followed by washing with water and drying, whereby 0.7 g (7.5 g in total) of the title compound was obtained.

Example 1

6-Cyano-1,1-(ethylenedioxy)-7-methyl-5-oxo-Δ6(8)-tetrahydroindolizine

To 7.5 g of the ketone (5) obtained in Preparation Example 8 were added 100 ml of acetonitrile and 30 ml of ethylene glycol to dissolve the former in the latter, followed by the addition of 10 ml of a boron trifluoride—ether complex salt. The resulting mixture was stirred at an external temperature of 50° C. for one hour. After the completion of the reaction, 1.0 g of activated charcoal was added to the reaction mixture and they were stirred for 30 minutes. From the reaction mixture, the activated charcoal was filtered off. The filtrate was evaporated under reduced pressure. To the crystals so precipitated, a mixture of methanol and isopropyl ether was added, followed by slurry stirring. The crystals were collected by filtration and then dried, whereby 6.4 g of the title compound were obtained.

Example 2

6-Cyano-1,1-(ethylenedioxy)- 7-methoxy-carbonyl)-methyll-5-oxo-Δ6(8)-tetrahydroindolizine To 300 mg of Compound (6) obtained in Example 1 were added 3 ml of dimethoxyethane and 0.4 ml of diethyl carbonate, followed by the addition of 220 ml of potassium t-butoxide. The resulting mixture was stirred at an external temperature of 95° C. for 2 hours under a nitrogen gas stream. After the completion of the reaction, the reaction mixture was poured into water, followed by the addition of acetic acid. The reaction mixture was extracted with chloroform. The chloroform layer was washed with a saturated aqueous solution of sodium bicarbonate, dried over magnesium sulfate and then evaporated under reduced pressure. The residue so obtained was recrystallized from chloroform-isopropyl ether, whereby 330 mg of the title compound were obtained.

Example 3

6-Cyano-1,1-(ethylenedioxy)-7-[(ethoxycarbonyl)-methyl]-5-oxo-Δ6(8)-tetrahydroindolizine To 300 mg of Compound (6) obtained in Example 1 were added 3 ml of dimethoxyethane and 0.4 ml of diethyl carbonate, followed by the addition of 130 mg of sodium ethoxide. The resulting mixture was stirred at an external temperature of 95° C. for 4 hours under a nitrogen gas stream. After the completion of the reaction, the reaction mixture was poured into water, followed by the addition of acetic acid. The resulting mixture was extracted with chloroform. The chloroform layer was washed with a saturated aqueous solution of sodium bicarbonate, dried over magnesium sulfate and then evaporated under reduced pressure. The residue so obtained was recrystallized from chloroform-isopropyl ether, whereby 210 mg of the title compound were obtained.

INDUSTRIAL APPLICABILITY

The present invention has made it possible to safely and easily prepare Compound (7) useful as an intermediate for the preparation of a camptothecin derivative (a) useful as an antitumor agent.

What is claimed is:

1. A process for the preparation of a compound represented by the following formula (7):

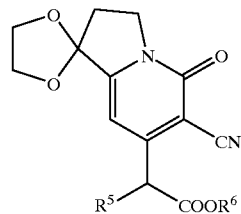

(7)

wherein $R^5$ represents a hydrogen atom or a $C_{1-5}$ alkyl group, and $R^6$ represents a $C_{1-6}$ alkyl, aryl group or aralkyl group, which comprises reacting a compound represented by the following formula (5):

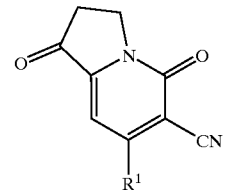

(5)

wherein $R^1$ represents a $C_{1-6}$ alkyl group with ethylene glycol in a solvent in the presence of a Lewis acid to obtain a compound represented by the following formula (6):

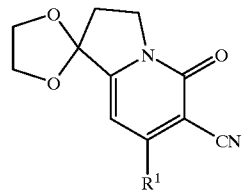

(6)

wherein $R^1$ has the same meaning as defined above and then reacting the resulting compound with a carbonate diester in a solvent in the presence of a metal alkoxide.

2. A process according to claim 1, wherein the compound represented by the formula (5) is obtained by reacting a compound represented by the following formula (1):

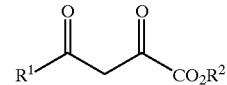

(1)

wherein $R^1$ represents a $C_{1-6}$ alkyl group and $R^2$ represents a $C_{1-6}$ alkyl group, aryl group or aralkyl group with an orthoformate ester in the presence of an acid catalyst to obtain a compound represented by the following formula (2):

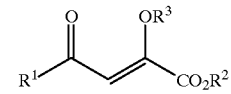

(2)

wherein $R^3$ represents a $C_{1-6}$ alkyl group, aryl group or aralkyl group and $R^1$ and $R^2$ have the same meanings as defined above, reacting the resulting compound with α-cyanoacetamide in a polar solvent in the presence of a base to obtain a compound represented by the formula (3):

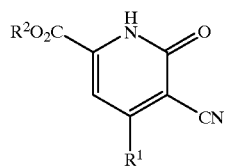

(3)

wherein $R^1$ and $R^2$ have the same meanings as defined above, or a salt thereof, reacting the resulting compound or salt with an acrylic ester to obtain a compound represented by the following formula (4):

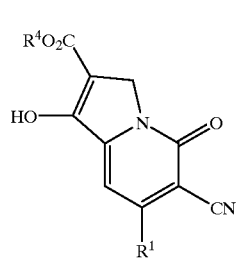

(4)

wherein $R^4$ represents a $C_{1-6}$ alkyl group and $R^1$ has the same meaning as defined above, and then subjecting the resulting compound to decarboxylation.

3. A process according to claim 1 or 2, wherein the Lewis acid is a boron trifluoride.

4. A process according to claim 1 or 2, wherein the solvent in which the compound represented by the formula (5) is dissolved is acetonitrile.

5. A process according to claim 1 or 2, wherein the metal alkoxide is potassium t-butoxide or sodium ethoxide.

6. A process according to claim 1 or 2, wherein the solvent in which the compound represented by the formula (6) is dissolved is an ether base solvent.

7. A process according to claim 1 or 2, wherein the solvent in which the compound represented by the formula (6) is dissolved is dioxane or dimethoxyethane.

8. A process according to claim 1 or 2, wherein $R^1$ represents a methyl group.

9. A process according to claim 1 or 2, wherein $R^1$ represents a propyl group.

10. A process according to claim 1 or 2, wherein $R^5$ represents a hydrogen atom.

11. A process according to claim 1 or 2, wherein $R^5$ represents an ethyl group.

12. A process according to claim 1 or 2, wherein all the steps starting from the compound of the formula (1) to the preparation of the compound of the formula (4) are carried out in a single reaction container.

13. A process according to claim 1 or 2, wherein the acid catalyst is an acid selected from the group consisting of sulfonic acid compounds and Lewis acid compounds.

14. A process according to claim 1 or 2, wherein the acid catalyst is an acid selected from sulfonic acid compounds.

15. A process according to claim 1 or 2, wherein the acid catalyst is methanesulfonic acid or p-toluenesulfonic acid.

16. A process according to claim 1 or 2, wherein the acid catalyst is p-toluenesulfonic acid.

17. A process according to claim 1 or 2, wherein the polar solvent is a compound selected from the group consisting of sulfoxide compounds, amide compounds and phosphoric amide compounds.

18. A process according to claim 1 or 2, wherein the polar solvent is dimethyl sulfoxide.

19. A process according to claim 1 or 2, wherein the base is a compound selected from the group consisting of alkali hydroxide compounds and alkali carbonate compounds.

20. A process according to claim 1 or 2, wherein the base is a compound selected from alkali carbonate compounds.

21. A process according to claim 1 or 2, wherein the base is potassium carbonate.

22. A process according to claim 1 or 2, wherein the acrylic ester is methyl acrylate.

\* \* \* \* \*